United States Patent [19]
Baserga et al.

[11] Patent Number: 5,643,788
[45] Date of Patent: Jul. 1, 1997

[54] METHOD OF INHIBITING THE PROLIFERATION AND CAUSING THE DIFFERENTIATION OF CELLS WITH IGF-1 RECEPTOR ANTISENSE OLIGONUCLEOTIDES

[75] Inventors: Renato Baserga, Ardmore; Christian Sell, Philadelphia; Raphael Rubin, Penn Valley, all of Pa.

[73] Assignee: Thomas Jefferson University, Philadelphia, Pa.

[21] Appl. No.: 479,173

[22] Filed: Jun. 6, 1995

Related U.S. Application Data

[63] Continuation of Ser. No. 158,761, Nov. 30, 1993, which is a continuation-in-part of Ser. No. 37,257, Mar. 26, 1993, abandoned.

[51] Int. Cl.$^6$ .............................. C12N 5/10; C07H 21/00; A61K 31/70; C12Q 1/68
[52] U.S. Cl. .............................. 435/325; 435/6; 435/91.1; 435/172.1; 435/172.3; 435/375; 536/24.3; 536/24.31; 536/24.32; 536/24.33; 536/24.5; 536/25.1; 514/44
[58] Field of Search .............................. 514/44; 536/24.5, 536/23.1, 24.3, 24.31, 24.32, 24.33, 25.1; 435/6, 91.1, 172.1, 172.3, 240.2

[56] References Cited

PUBLICATIONS

E. Uhlmann et al., Chemical Reviews 90 (4) (Jun. 1990) 543–584.
C. Stein et al., Science 261 (Aug. 20, 1993) 1004–12.
B. Tseng et al., Cancer Gene Therapy 1 (1) (Mar. 1994) 65–71.
P. Westermann et al., Biomed. Biochim. Acta 48 (1) ('89) 85–93.
J. Milligan et al., J. Med. Chem. 36 (14) (Jul. 9, 1993) 1923–37.
K. Culver et al., TIG 10 (5) (May 1994) 174–78.
V. Dzau et al., TIBTECH 11 (May 1993) 205–210.
P. Hug et al., Biochim. Biophys. Acta 1097 ('91) 1–17.
R. Weiss, Science News, 139 (Feb. 16, 1991) 108–9.
D. Marcola et al., B.B.R.C. 147 (1) (Aug. 1987) 288–94.
Z. Pietrzkowski et al., Cancer Res. 53 (Mar. 1, 1993) 1102–6.
Z. Pietrzkowski et al., Mol. Cell. Biol. 12 (9) (Sep. 1992) 3883–9.
Z. Pietrzkowski et al., Cell Growth & Diff. 3 (Apr. 1992) 199–205.
P. Poreu et al., Mol. Cell Biol. 12 (11) ('92) 5069–77.
D. Becker et al., EMBO J. 8(12) ('89) 3685–91.
A. Ullrich et al., EMBO J. 5(10) ('86) 2503–12.
F. Talavera et al., Cancer Res. 50 (May 15, 1990) 3019–24.
H. Lahm et al., EACR-XI Mtg./Eur. J. Cancer, vol. 27, Suppl. 3 (Nov. '91) p. 579.
E. Wickstrom et al., FASEB J., vol. 5 (5) (Mar. 15, 1991) p. A1443.
J. Holt et al. PNAS 83 (Jul. 1986) 4794–8.
S. Loke et al. Curr. Topics in Microbiol & Immunol., vol. 141 ('88) pp. 282–289.

*Primary Examiner*—Charles C.P. Rories
*Attorney, Agent, or Firm*—Cooley Godward LLP

[57] ABSTRACT

A method of inhibiting the proliferation and causing the differentiation of undifferentiated cells comprising contacting the undifferentiated cells with an effective amount of an antisense oligonucleotide having a sequence which is complementary to a region of the IGF-1 receptor RNA. The sequence of the antisense oligonucleotide is selected from an oligodeoxynucleotide sequence complementary to codons −29 to −24 of the signal sequence of the IGF-1 receptor and an oligoribonucleotide sequence complementary to codons 1 to 309 of the sequence of the IGF-1 receptor. The oligoribonucleotide sequence may be provided by an expression vector.

4 Claims, 12 Drawing Sheets

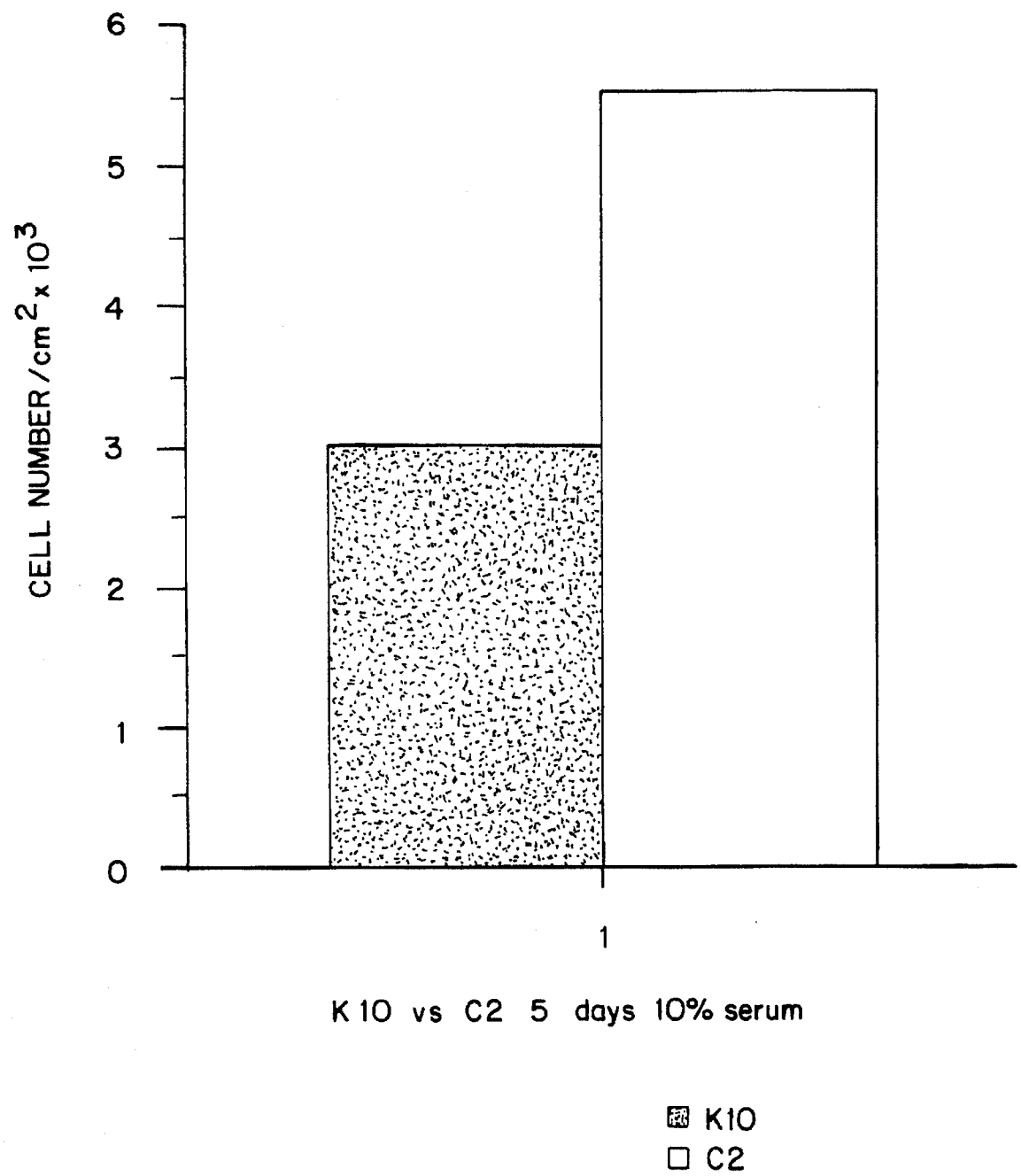

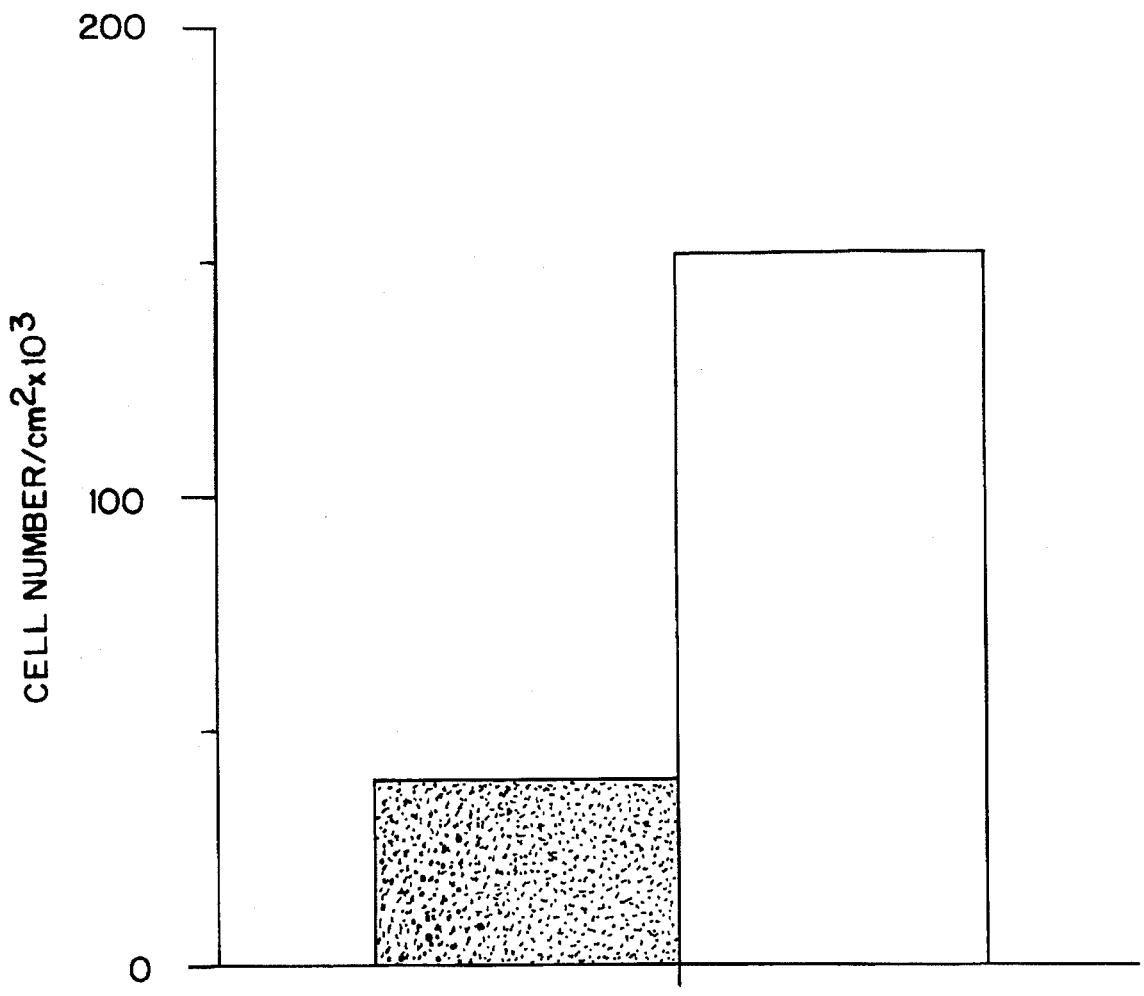

```
                                                                              -30
                                                                              MetLysSerGlyGlySerGlyGlySerPro
TTTTTTTTTTTTGAGAAAGGGAATTTCATCCCAAATAAAAGGAATGAAGTCTGGCTCCGGAGGAGGGTCCCCG
    -20                                                       -1 1→ α subunit
    ThrSerLeuTrpGlyLeuLeuPheLeuSerAlaAlaAlaLeuSerLeuPheProThrSerGlyIleGluIleGluGlyLysIleGlyPro
    ACCTCGCTGTGGGGGCTCCTCGTTTCTCCGGCGGCGCTCTCGCTGCTGCCGACGAGTGGAGAAATCGCGGGCCA           150

-10                                                             1           30
         GlyIleAspIleArgAsnAspTyrGlnInLeuLysArgLeuGluAsnCysThrValIleGluGlyTyrLeuHis
         GGCATCGACATCCGCAACGACTATCAGCAGCTGAAGCGCCTGGAGAACTGCACGGTGATCGAGGGCTACCTCCAC 10                                       20
                  IleLeuLeuIleSerLysAlaGluAspTyrArgSerTyrArgPheProLysLeuThrValIleThrGluTyrLeu
                  ATCCTGCTCATCTCCAAGGCCGAGGACTACCGCAGCTATCGCTTCCCCAAGCTCACGGTCATTACCGAGTACTTG           300
                         60                                          70                 80
                                                                                  LeuPheArgValAlaGlyLeuGluSerLeuGlyAspLeuPheProAsnLeuThrValIleArgGlyTrpLys
                                                                                  CTGCTGTTCCGAGTGGCTGGCCTCGAGAGCCTCGGGGATCTCTTCCCCAACCTCACGGTCATCCGGGCTGGAAA 90                                                     100
                                                                                  LeuPheTyrAsnTyrAlaLeuValIlePheGluMetThrAsnLeuLysAsnAlaAspLeuCysTyrLeuSerThrValAspTrpSerLeuIle
                                                                                  CTCTTCTACAACTACGCCCTGGTCATCTTCGAGATGACCAATCTCAAGAATGCTGACCTCTGTTACCTCTCCACTGTGGACTGGTCCCTGATC           450
                                                                                          110                                                        120                       130
                                                                                  IleThrArgGlyAlaIleArgIleGluLysAsnAlaAspLeuCysTyrLeuSerThrValAspTrpSerLeuIle
                                                                                  ATTACTCGGGGGGCCATCAGGATTGAGAAAAATGCTGACCTCTGTTACCTCTCCACTGTGGACTGGTCCCTGATC

LeuAspAlaValSerAsnAsnTyrIleValGlyAsnLysProProLysGluCysGlyAspLeuCysProGlyThr
                                                                                  CTGGATGCGGTGTCCAATAACTACATTGTGGGGAATAAGCCCCCAAAGGAATGTGGGGACCTGTGTCCAGGGACC           600
                                                                                          140                                                        150
                                                                                          160                                                        170             180
                                                                                  MetGluGluLysProMetCysGluLysThrThrIleAsnAsnGluTyrArgCysTrpThrThrAsnArg
                                                                                  ATGGAGGAGAAGCCGATGTGTGAGAAGACCACCATCAACAATGAGTACAGGTGCTGGACCACAAACCGC
```

FIG. 7A

```
        CysGlnLysMetCysProSerThrCysGlyLysArgAlaCysThrGluAsnAsnGluCysCysHisProGluCys
        TGCCAGAAAATGTGCCCCAAGCACACGTGTGGGAAGAGCGCGGGCTGCACCGAGAACAATGAGTGCTGCCACCCCGAGTGC  750
                         190                200                                    230
                210                       220
        LeuGlySerCysSerAlaProAspAsnAspAlaCysValAlaCysArgHisTyrTyrAlaGlyValCys
        CTGGGCAGCTGCAGCGCGCCTGACAACGACGCCTGTGTAGCTTGCCGCCACTACTACGCCGGTGTCTGT
                                                                                     900
                                                                   250
        ValProAlaCysProProAsnThrTyrArgPheGluGlyTrpArgCysValAspArgAspPheCysAlaAsnIle
        GTGCCTGCCTGCCCGCCCAACACCTACAGGTTTGAGGGCTGGCGCTGTGTGGACCGTGACTTCTGCGCCAACATC
                 260                        270                        280
        LeuSerAlaGluSerSerAspSerGluGlyPheValIleHisAspIleHisArgProArgGluCysProSerGly
        CTCAGCGCCGAGAGCAGCGACTCCGAGGGGTTTGTGATCCACGACATCCACAGGCCGAGGGAGTGCCCCTCGGGC
                                           290                       300
        PheIleArgAsnGlySerGlnSerMetTyrCysIleProCysGluGlyProCysProLysValCysGluGluGlu
        TTCATTCGCAACGGCAGCCAGAGCATGTACTGCATCCCCTGTGAAGGTCCTTGCCCGAAGGTCTGTGAGGAAGAA  1050
                                                        310                     330
                320
        LysLysThrLysAspSerValThrSerAlaGlnMetLeuGlnGlyCysThrIlePheLysGlyAsnLeu
        AAGAAAACAAAGGACAGTGTTACTTCTGCTCAGATGCTCCAAGGATGCACCATCTTCAAGGGCAATTTG
                                                     350
                                                                          380
        LeuIleAsnIleArgArgGlyAsnAsnIleAlaSerGluLeuGluAsnPheMetGlyLeuIleGluValValThr
        CTCATTAACATCCGACGGGGAAATAACATTGCTTCAGAGCTTGAGAACTTCATGGGCCTCATCGAGGTGGTGACG  1200
                                           350
                                        370
        GlyTyrValLysIleArgHisSerHisAlaLeuValSerLeuPheLeuLysAsnLeuArgLeuIleLeuGly
        GGCTACGTGAAGATCCGGCATTCTCATGCCCTTGTCTCCCTGTTCCTTAAAAACCTTCGCCTCATCCTAGGA
                                                                              380
                390
        GluGluGluLeuGlyTyrValLeuAspAsnGlnAsnLeuGlnLeuTrpAspAsp
        GAGGAGGAGCTAGGATACGTCCTGGACAACCAGAACTTGCAGCAACTGTGGGAC  1350
                                          400
```

FIG. 7B

```
                                                                          430
            410                  420                              |
  HisArgAsnLeuThrIleLysAlaGlyLysMetTyrPheAlaAsnProLysLeuCysValSerGluIleTyr
  CACCGCAACCTGACCATCAAAGCAGGGAAAATGTACTTTGCTTTCAATCCCAAATTATGTTTCCGAAATTTAC 440                              450
  ArgMetGluValThrGlyThrLysGlyArgGlnSerLysGlyAspIleAsnThrArgAsnAsnGlyGluArg     1500
  CGCATGGAGGAAGTGACGGGGACTAAAGGGCGCCAAAGCAAAGGGGACATAAACACCAGGAACAACGGGGAGAGA 460                        470                    480
  AlaSerCysGluSerAspValLeuHisPheThrSerThrThrSerLysAsnArgIleIleIleThrTrpHis
  GCCTCCTGTGAAAGTGACGTCCTGCATTTCACCTCCACCACCAGTCGAAGAATGCATCATAACCTGGCAC 490                              500
  ArgTyrArgProProAspTyrArgAspIleSerPheThrValTyrLysGluAlaProPheLysAsnVal       1650
  CGGTACCGGCCCCCCTGACTACAGGGATCTCAGCTTCACCGTTTACAAGGAAGCACCCTTTAAGAATGTC 510                    520                              530
  ThrGluTyrAspGlyGlnAspAlaCysGlySerAsnSerTrpAsnMetValAspValAspLeuProAsnLys
  ACAGAGTATGATGGGCAGGATGCCTGCGGCTCCAACAGCTGGAACATGGTTGACGTTGACCTCCCGCCAACAAG

540
  AspValGluProGlyIleLeuHisGlyLeuLeuLysSerGlyAlaAlaLysSerGluIleLeuTyrIleArgThrValLysAlaValThr    1800
  GACGTGGAGCCCGGCATCTTACTAGACATATCCGTGGGGCAAGAGTGAGATCTTGTACATTCGCACCGTGTACAAGGCTGTGACC 560                              570                              580
  LeuThrMetValGluAsnAspHisIleArgGlyAlaLeuSerAsnSerSerGlnLeuIleValLysSerGlnLeuIleValLysSerValValValValValArgThrAsnAlaSerVal
  CTCACCATGGTTGAGAACGACCATATCCGTGGGGCTCAAGAGTGAGATCTTGTACATTCGCACCATGCTTCAGTT 590                              600
  ProSerIleProLeuAspValLeuSerAlaSerArgAsnSerSerGlnLeuLeuValLysTrpAsnProProSer     1950
  CCTTCCATTCCTTGGACGTTCTTTCAGCATGCATCGAACTCCTCTTCAGTTAATGTGAAGTGGAACCCCTCT 610                              620                     630
  LeuProAsnGlyAsnLeuSerTyrTyrIleValArgTrpGlnArgGlnProGlnAspGlyTyrLeuTyrArgHis
  CTGCCCAACGGCAACCTGAGTTACTACATTGTCGCTAGGCAGCCTCAGGAGGCTACCTTTACCGGCAC
```

FIG. 7C

```
                    640                          650
AsnTyrCysSerLysAspLysIleProIleArgLysTyrAlaAspGlyThrIleAspIleGluValThrGlu
AATTACTGCTCCAAAGACAAAAATCCCATCAGGAAGTATGCCGACGGCACCATCGACATTGAGGAGGTCACAGAG          2100
    660                          670                            680
AsnProLysThrGluValCysGlyGlyGluLysGlyProLysThrGluAlaGluLysGln
AACCCCAAGACTGAGGTGTGTGGTGGGGAGAAAGGGCCTAAAACTGAAGCCGAGAAGCAG                         2250
                                700
AlaGluLysGluAlaAlaGluTyrArgLysValPheGluAsnPheLeuHisAsnSerIleProArgPro
GCCGAGAAGGAGGCTGAATACCGCAAAGTCTTTGAGAATTTCCTGCACAACTCCATCTTCGTGCCAGACCT              
                     710                720                          730
GluArgLysArgArgAspValMetGlnValAlaAlaAsnThrThrAlaAla
GAAAGGAAGCGGGAGGATGTCATGCAAGTGGCAGCCAACACCACGGCCGCA
        β subunit                                                                    2400
                740
AspThrTyrAsnIleThrAspProGluLeuGluThrGluTyrProPhePheGluSerArgValAspAsnLys
GACACCTACAACATCACCGACCCGGAAGAGCTACCCTTTCTTGAGAGCAGAGTGGATAACAAG                      
          760                 770                       780
GluArgThrValIleSerAsnLeuArgProPheThrLeuTyrArgIleAspIleValTyrCysAsnHisGluAla
GAGAGAACTGTGTCATTCTAACCTTCGGCCCTTTCACATTGTACCGCATCGATATCGTCAGCTGCAACCACGAGGCT       
              790                    800
GluLysLeuGlyCysSerAlaSerAsnPheValPheAlaArgThrMetProAlaGluGlyAlaAspAspIlePro
GAGAAGCTGGGCTGCAGCGCCTCCAACTTCGTCTTTGCAAGGACTATGCCCGCAGAAGGAGCAGATGACATTCCT        2550
          810                        820                      830
GlyProValThrTrpGluProArgProGluAsnSerIlePheLysTrpProGluProGluAsnProAsnGly
GGGCCAGTGACCTGGGAGCCAAGGCCTGAAAACTCCATCTTTTAAAGTGGCCGGAACCTGAGAATCCCAATGGA          
                                    850
LeuIleLeuMetTyrGluIleLysTyrGlySerGlnValGluAspGlnArgGluCysValSerArgGlnGluTyr
TTGATTCTAATGTATGAAATAAAATACGGATCACAAGTTGAGGATCAGAGGGAGAATGTGTGTCCAGAGACAGGAATAC     2700
```

FIG. 7D

```
                860                                                870                                                880
ArgLysTyrGlyIleAlaLysLeuAsnArgLeuAsnArgProGlyAsnTyrThrAlaArgIleGlnAlaThrSerLeu
AGGAAGTATGGGATTGCAAAGCTGAATCGGCTAAACCGGGGAACTACACAGCCCGGATTCAGGCCACATCTCTC            2850
                              890                                                900
SerGlyAsnGlySerThrTrpThrAspProValPhePheTyrValGlnAlaLysThrGlyTyrGluAsnPheIleHis
TCTGGGAATGGGTCGTGGACAGATCCTGTGTTCTTCTATGTCCAAGCCAAAACAGGATATGAAAACTTCATCCAT
                910                                                920                                                930
LeuIleIleAlaLeuProValAlaValLeuLeuIleValGlyGlyLeuValValIleMetLeuTyrValPheHisArg
CTGATCATCGCTCTGCCCGTCGCTGTCCTGTTGATCGTGGGAGGGTTGGTTGATTATGCTGTACGTCTTCCATAGA       3000
                                940                                                950
LysArgAsnAsnSerArgLeuGlyAsnGlyValLeuTyrAlaSerValAsnProGluTyrPheSerAlaAlaAsp
AAGAGAAATAACAGCAGGCTGGGGAATGGAGTTCTGTATGCCTCTGTGAACCCGGAGTACTTCAGCGCTGCTGAT
                960                                                970                            980
ValTyrValProAspGluTrpGluValAlaArgGluLeuLysIleThrMetSerArgGluLeuGlyGlnGlySerPhe
GTGTACGTTCCTGATGAGTGGGAGGTGGCTCGGGAGAGATCACCATGAGCCGGGAACTTGGGCAGGGGTCGTTT
                                                          990                                                1000
                                                        *                                                           *  →
GlyMetValTyrGluGlyValValAlaLysGlyValValLysAspGluProGluThrArgValAlaIleLysThrVal
GGGATGGTCTATGAAGGAGTTGTGGCCAAGGGTGTGGTGAAAGATGAACCTGAAACCAGAGTGGCCATTAAAACAGTG   3150
                        1010                                                1020                                                1030
AsnGluAlaAlaSerMetArgGluIleGluPheLeuAsnGluAlaSerValMetLysGluPheAsnCysHis
AACGAGGCCGCAAGCATGCGTGAGAGGATTGAGTTTCTCAACGAAGCTTCTGTGATGAAGGAGTTCAATTGTCAC
                1040                                                1050
HisValValArgLeuLeuGlyValValSerGlnGlyGlnProThrLeuValIleMetGluLeuMetThrArgGly
CATGTGGTGCGATTGCTGGGTGTCCAAGGCCAACACTGGTCATCATGGAACTGATGACACGGGGC            3300
                1060                                                1070                                    1080
AspLeuLysSerTyrLeuArgSerLeuArgProGluMetGluAsnAsnProValLeuAlaProProSerLeuSer
GATCTCAAAAGTTATCTCCGGTCTCTGAGGCCAGAAATGGAGAATAATCCAGTCCTAGCACCTCCAAGCCTGAGC
```

```
                    1310                        1320
LeuArgAlaSerPheAspGluArgGlnProTyrAlaHisMetAsnGlyGlyArgLysAsnGluArgArgAlaLeuPro
CTCCGGGCCAGCTTCGACGAGAGACAGCCCTTACGCCCACATGAACGGGGCCGCAAGAACGAGCGGGCCTTGCCG    4200

LeuProGlnSerThrCysEnd
CTGCCCCAGTCTTCGACCTGCTGATCCTTGGATCCTGTGCAAACAGTAACGTGTGCGCACGGCAGCGG            4350
GGTGGGGGGGAGAGAGAGTTTTAACAATCCATTCACAAGCCCTCCTGTACCTCAGTCTTCAGTTCTGCCCT         4500
TGCTGCCCGCGGGAGACAGCTTCCTGCAGTAAAACACATTTGGGATGTTCCTTTTTCAATATGCAAGCAGCTT       4650
TTATTCCCTGCCCAAACCCTTAACTGACATGGGCCTTTAAGAACCTTAATGACAACACTTAATAGCAACAGAGC      4800
ACTTGAGAACCAGTCTCCTCACTCTGTCCCTGTTCTCCCTGTCCCTTTCTCCCTCTCCTGTTCATAAC            4950
GGAAAAATAATTGCCACAGTCCAGCTGGGAAGCCCTTTTATCAGTTTGAGGAAACGTGGAGATGGAAATTTTTACCT   4989
ATCCAACCACTGTACACACCGGCCTGACACAGTCGGGACATGAAATTTACAAAGGGCCATCGTTCATCCAAGCTGTTACCATTTTAACGC
TTATCTTTCACCTTTTCTAGGGACATGAAATCCTGAACTTTCCCTTCCCATCGGCCCTGATTCCTCGTCCGGAGGCATGGG
TGCCCTAATTTTGCCAAAATCCTGAACTTTCCATTTGAGAGACACAGGTCTCCATTGCTTCTGACTAGATTATTATTTGGGGAACTGGACACAATAG
TGAGCATGGCAGCTGGTTGCTCCATTTGAGAGACACAGGTCTCCATTGCTTCTGACTAGATTATTATTTGGGGAACTGGACACAATAG
GCTGCTCAAGGCCACAGGCACACAGGTCTCCATTGCTTCTGACTAGATTATTATTTGGGGAACTGGACACAATAG
GTCTTTCTCAGTGAAGGTGGGGAGAAGCTGAACCGGC
```

FIG. 7G

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

ACCATTGATT CTGTTACTTC                          20

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:2:

ATACTCTGTG ACATTCTTAA                          20

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

CTGCTCCTCT CCTAGGATGA                          20

( 2 ) INFORMATION FOR SEQ ID NO:4:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:4:

TCCTCCGGAG CCAGACTT                            18

( 2 ) INFORMATION FOR SEQ ID NO:5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:5:

AAGTCTGGCT CCGGAGGA 18

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GCACCGGGAA GTTGTGTCAA 20

(2) INFORMATION FOR SEQ ID NO:7:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
CTTTGTTTTC TTTTCTTCCT CACAGACCTT CGGGCAAGGA CCTTCACAAG      50
GGATGCAGTA CATGCTCTGG CTGCCGTTGC GGATGAAGCC CGAGGGCAC      100
TCCTGCATGC ACTCGCCGTC GTGGATCACA AACCCCTCGG AGTCGCTGCT    150
CTCGGCGCTG AGGATGTTGG CGCAGAAGTC ACGGTCCACA CAGCGCCAGC    200
CCTCAAACCT GTAGGTGTTG GGCGGGCAGG CAGGCACACA GACACCGGCA    250
TAGTAGTAGT GGCGGCAAGC TACACAGGCC GTGTCGTTGT CAGGCGCGCT    300
GCAGCTGCCC AGGCACTCGG GGTGGCAGCA CTCATTGTTC TCGGTGCACG    350
CCCGCTTCCC ACACGTGCTT GGGCACATTT TCTGGCAGCG GTTTGTGGTC    400
CAGCAGCGGT AGTTGTACTC ATTGTTGATG GTGGTCTTCT CACACATCGG    450
CTTCTCCTCC ATGGTCCCTG GACACAGGTC CCCACATTCC TTTGGGGGCT    500
TATTCCCCAC AATGTAGTTA TTGGACACCG CATCCAGGAT CAGGGACCAG    550
TCCACAGTGG AGAGGTAACA GAGGTCAGCA TTTTTCACAA TCCTGATGGC    600
CCCCCGAGTA ATGTTCCTCA GGTTGTAAAG CCCAATATCC TTGAGATTGG    650
TCATCTCGAA GATGACCAGG GCGTAGTTGT AGAAGAGTTT CCAGCCGCGG    700
ATGACCGTGA GGTTGGGGAA GAGGTCTCCG AGGCTCTCGA GGCCAGCCAC    750
TCGGAACAGC AGCAAGTACT CGGTAATGAC CGTGAGCTTG GGGAAGCGGT    800
AGCTGCGGTA GTCCTCGGCC TTGGAGATGA GCAGGATGTG GAGGTAGCCC    850
TCGATCACCG TGCAGTTCTC CAGGCGCTTC AGCTGCTGAT AGTCGTTGCG    900
GATGTCGATG CCTGGCCCGC AGATTTC                              927
```

(2) INFORMATION FOR SEQ ID NO:8:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:8:

| | | | | | |
|---|---|---|---|---|---|
| CUUUGUUUUC | UUUUCUUCCU | CACAGACCUU | CGGGCAAGGA | CCUUCACAAG | 50 |
| GGAUGCAGUA | CAUGCUCUGG | CUGCCGUUGC | GGAUGAAGCC | CGAGGGGCAC | 100 |
| UCCUGCAUGC | ACUCGCCGUC | GUGGAUCACA | AACCCCUCGG | AGUCGCUGCU | 150 |
| CUCGGCGCUG | AGGAUGUUGG | CGCAGAAGUC | ACGGUCCACA | CAGCGCCAGC | 200 |
| CCUCAAACCU | GUAGGUGUUG | GGCGGGCAGG | CAGGCACACA | GACACCGGCA | 250 |
| UAGUAGUAGU | GGCGGCAAGC | UACACAGGCC | GUGUCGUUGU | CAGGCGCGCU | 300 |
| GCAGCUGCCC | AGGCACUCGG | GGUGGCAGCA | CUCAUUGUUC | UCGGUGCACG | 350 |
| CCCGCUUCCC | ACACGUGCUU | GGGCACAUUU | UCUGGCAGCG | GUUUGUGGUC | 400 |
| CAGCAGCGGU | AGUUGUACUC | AUUGUUGAUG | GUGGUCUUCU | CACACAUCGG | 450 |
| CUUCUCCUCC | AUGGUCCCUG | GACACAGGUC | CCCACAUUCC | UUUGGGGGCU | 500 |
| UAUUCCCCAC | AAUGUAGUUA | UUGGACACCG | CAUCCAGGAU | CAGGGACCAG | 550 |
| UCCACAGUGG | AGAGGUAACA | GAGGUCAGCA | UUUUUCACAA | UCCUGAUGGC | 600 |
| CCCCCGAGUA | AUGUUCCUCA | GGUUGUAAAG | CCCAAUAUCC | UUGAGAUUGG | 650 |
| UCAUCUCGAA | GAUGACCAGG | GCGUAGUUGU | AGAAGAGUUU | CCAGCCGCGG | 700 |
| AUGACCGUGA | GGUUGGGGAA | GAGGUCUCCG | AGGCUCUCGA | GGCCAGCCAC | 750 |
| UCGGAACAGC | AGCAAGUACU | CGGUAAUGAC | CGUGAGCUUG | GGAAGCGGU | 800 |
| AGCUGCGGUA | GUCCUCGGCC | UUGGAGAUGA | GCAGGAUGUG | GAGGUAGCCC | 850 |
| UCGAUCACCG | UGCAGUUCUC | CAGGCGCUUC | AGCUGCUGAU | AGUCGUUGCG | 900 |
| GAUGUCGAUG | CCUGGCCCGC | AGAUUUC | | | 927 |

METHOD OF INHIBITING THE PROLIFERATION AND CAUSING THE DIFFERENTIATION OF CELLS WITH IGF-1 RECEPTOR ANTISENSE OLIGONUCLEOTIDES

CROSS REFERENCE TO RELATED APPLICATIONS

This application is a continuation of U.S. application Ser. No. 08/158,761, filed Nov. 30, 1993, now abandoned, which is a continuation in part of U.S. application Ser. No. 08/037,257, filed Mar. 26, 1993, now abandoned.

INTRODUCTION

This invention was funded by National Institute of Health Grants GM 33694 and CA 56309. The U.S. government may have certain rights in the invention.

BACKGROUND OF THE INVENTION

The IGF-1 receptor is expressed in many cell types including fibroblasts, epithelial cells, smooth muscle cells, chondrocytes, osteoblasts and several lineages of hemopoietic cells which have IGF-1 receptors and an absolute requirement for IGF-1 for growth in cultures. A review of human cells expressing the IGF-1 receptor and requiring IGF-1 for growth can be found in Baserga and Rubin, *Critical Reviews in Eukaryote Gene Expression*, 1993, 3: 47–61; and Goldring and Goldring, *Eukaryote Gene Expression* 1991, 1, 301–326. Macaulay, *Br. J. Cancer* 1992, 65,311–320, has reviewed the expression of insulin-like growth factors (both IGF-1 and IGF-2) and their receptors in human cancer. Recently, it was shown that IGF-1 peptide analogs may be useful for inhibiting the growth of IGF-1 dependent cells (Pietrzkowski et al., *Cancer Res.* 1993, 53, 1102–1106). Antisense oligonucleotides to mRNA coding for IGF-1 was used to transform rat glioblastoma cells. The cells reversed the transformed phenotype, and acted immunogenic against the parent glioblastoma cell line, completely inhibiting its growth. Trojan et al. *Science*, 1993, 259, 94–97 and Trojan et al., *Proc. Natl. Acad. Sci. U.S.A.*, 1992, 89, 4874–4878. However, effective methods of inhibiting growth and causing differentiation of cells are still greatly desired.

SUMMARY OF THE INVENTION

Methods of inhibiting the growth and causing differentiation of undifferentiated cells with antisense oligonucleotides complementary to a region of the IGF-1 receptor are provided. The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include DNA sequences; and antisense RNA oligonucleotides produced from an expression vector. Each of the antisense oligonucleotides of the present invention are complementary to regions of the IGF-1 receptor sequence. The antisense oligodeoxynucleotide of the present invention comprises a sequence complementary to codons −29 to −24 of the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribonucleotide, SEQ ID NO: 8 produced from an expression vector comprises a sequence complementary to codons 1 to 309 of the IGF-1 receptor, FIG. 7. See Ullrich et al., *EMBO J.*, 1986, 5:2503 Contemplated by this definition are fragments of oligos within the coding sequence for the IGF-1 receptor.

BRIEF DESCRIPTION OF THE FIGURES

FIG. 5(A and B). Panel A is a schematic representation of cell growth of K10 and C2 cells in 10% serum after 5 days. FIG. 5, Panel B is a schematic representation of K10 and C2 cells transfected with T antigen (K10a58 and C2a58 respectively). The K10 cells have not been fully transformed.

FIG. 7 provides the amino acid and nucleotide sequence of IGF-1 receptor.

DETAILED DESCRIPTION OF THE INVENTION

Figure 1A:
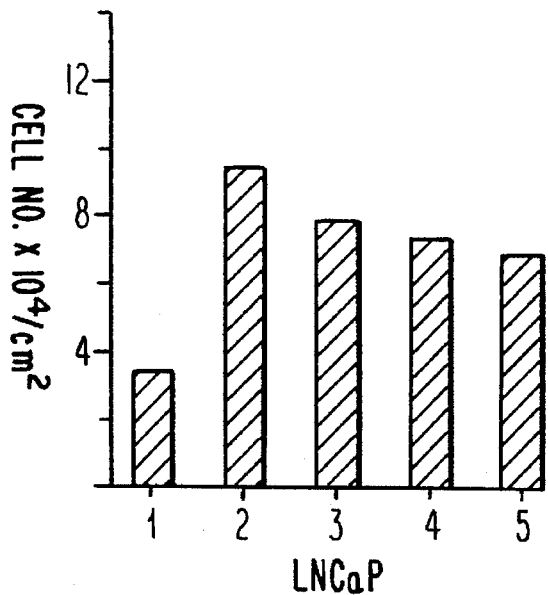
FIG. 1 is a schematic representation of the effect of individual growth factors on the growth of prostatic cancer cell lines (abscissa). Bars: 1–48 hours after plating; 2—no additions (96 hours after plating); 3—epidermal growth factor (EGF) (20 ng/ml, 96 hours after plating); 4—insulin-like growth factor (IGF-1) (20 ng/ml, 96 hours after plating); 5—platelet derived growth factor (PDGF) (1 ng/ml, 96 hours after plating).

Methods of inhibiting the proliferation of and causing the differentiation of undifferentiated cells are provided by the present invention. In one embodiment, an antisense oligonucleotide having a sequence complementary to codons −29 to −24 of the signal sequence of the IGF-1 receptor was found to be effective.

For purposes of the present invention, undifferentiated cells include and are not limited to transformed cells, cancer cells, prostate cancer cells, ovarian cancer cells, mammary cancer cells, lung cancer cells, glioblastoma cells, smooth muscle cells, bone marrow stem cells, hematopoietic cells, osteoblasts, epithelial cells, fibroblasts. Abnormal cells are cells which do not grow in accordance with the predicted patterns of a selected cell type, including and not limited to cancer cells such as those identified above, and transformed cells.

For purposes of the current invention, mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Figure 7F:
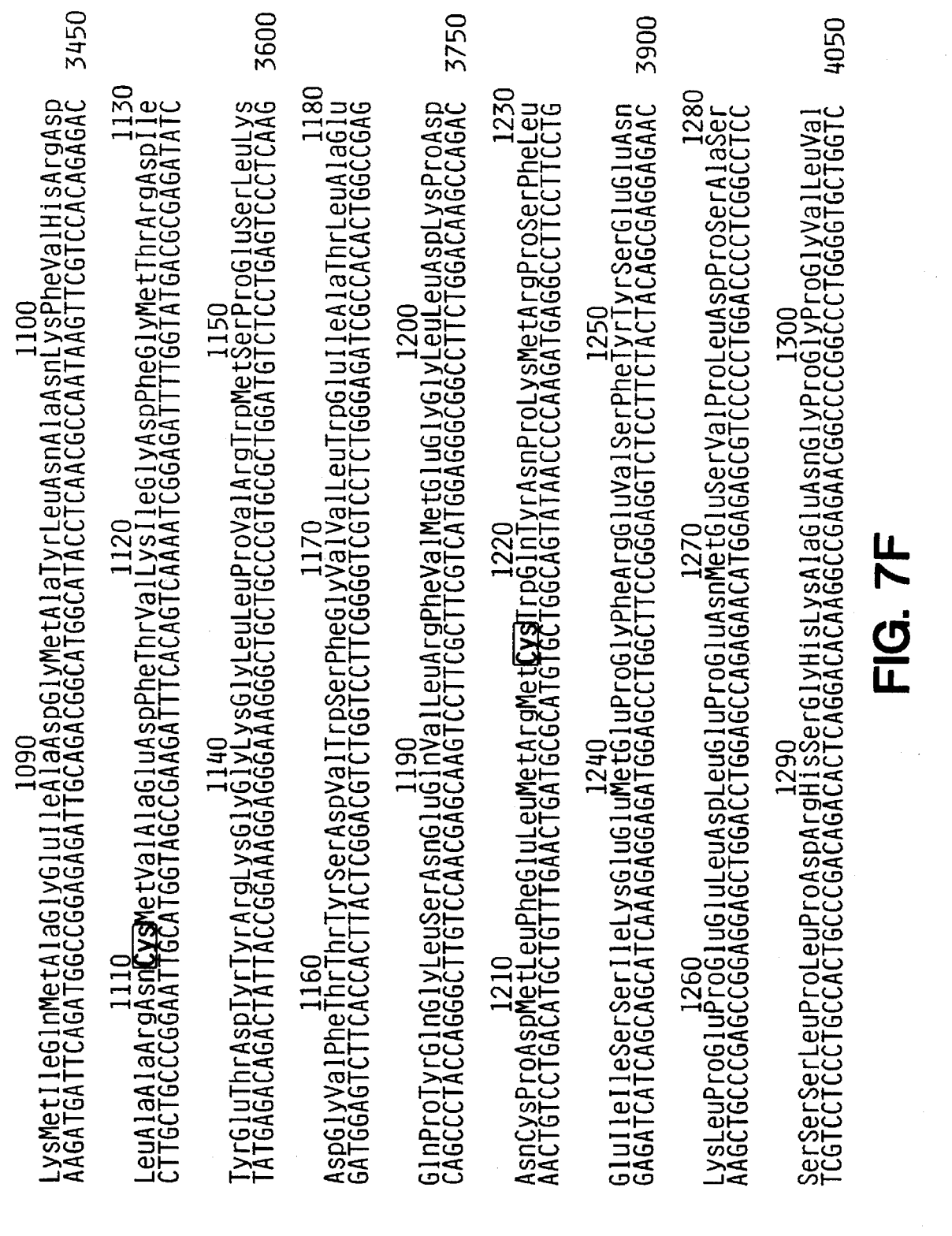

The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include single stranded DNA sequence and an antisense RNA oligonucleotide produced from an expression vector. Each of the antisense oligonucleotides of the present invention are complementary to regions of the IGF-1 receptor sequence. The antisense oligodeoxynucleotide of the present invention comprises a sequence complementary to codons −29 to −24 of the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribonucleotide, SEQ ID NO: 8 produced from an expression vector comprises a sequence complementary to codons 1 to 309 of the IGF-1 receptor, FIG. 7. See Ullrich et al., *EMBO J.*, 1986, 5:2503. Contemplated by this definition are fragments of oligos within the coding sequence for the IGF-1 receptor. In addition, mismatches within the sequences identified above, which achieve the methods of the invention, such that the mismatched sequences are substantially complementary to the IGF-1 sequences identified above, are also considered within the scope of the disclosure. Mismatches which permit substantial complementarity to the IGF-1 sequences will be known to those of skill in the art once armed with the present disclosure. The oligos may also be unmodified or modified.

The present invention is also directed to a method of treating mammals having cancer comprising contacting the mammal with an effective amount of an antisense oligonucleotide having a sequence which is complementary to a region of the IGF-1 receptor RNA. Cancer cells contemplated by the present invention include and not limited to those identified above.

Methods of administering the antisense oligos of the present invention include techniques well known in the art such as and not limited to liposomes, plasmid expression, retroviral vectors, splicing an oligo to another sequence such as a promoter or a growth factor, wherein the plasmid and/or vector is transfected with an expression plasmid expressing the antisense oligonucleotide, exposing cells to a medium or wash containing the oligo. In the administration of oligos via vectors or plasmids, a non-coding RNA strand of IGF-1 receptor is preferably used in order to produce antisense RNA oligos which are expressed by the cell. The RNA oligos then bind IGF-1 sense or coding RNA sequence. Accordingly, an oligo RNA sequence similar to SEQ ID NO: 4 is used. In the administration of a medium or wash, antisense DNA is preferably used an oligo DNA, similar to SEQ ID NO: 4 and SEQ ID NO: 7.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting IGF-1 receptors at the same time. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa. The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty µg/ml antisense oligo was used for in vitro methods of providing oligos in media for cell growth in culture. This concentration may be extrapolated for in vivo use. The concentration of antisense oligodeoxynucleotides for in vivo use is about 40µ/g body weight. The in vivo use of the expression vector expressing RNA oligonucleotides is determined by the number of transfected cells.

The growth of prostatic cancer cell lines was inhibited by antisense oligonucleotides to IGF-1 receptor RNA indicating that these cells need a functionally activated IGF-1 receptor for growth. These compositions are nontoxic at the concentrations used and are very effective and easy to deliver. These compositions may be useful in the treatment of prostatic cancer and other forms of abnormal growth because IGF-1 is a required growth factor for a wide variety of cell types and its action seems to be located downstream from other growth factors receptors. Therefore, while cells could circumvent other growth factor requirements by establishing an IGF-1/IGF-1 receptor autocrine loop, for many cell types, the activation of the IGF-1 receptor is the last receptor-mediated event before DNA synthesis and mitosis, and, presumably cannot be circumvented except by intracellular substrates of the IGF-1 receptor. Methods of reversing the transformed phenotype of cells with abnormal growth potential are also provided.

Figure 1B:
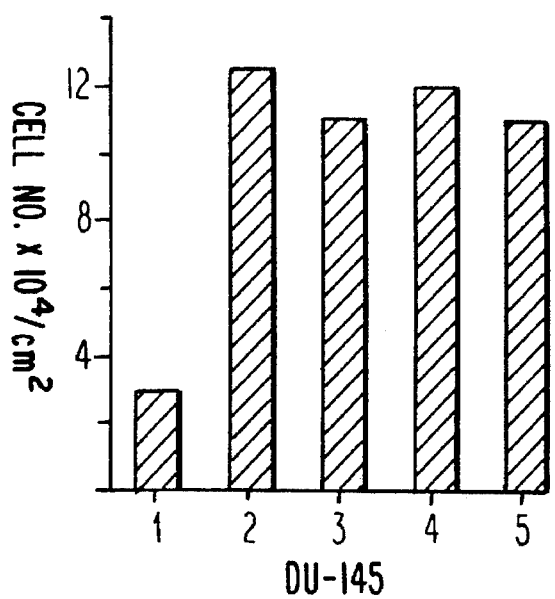
Figure 1C:
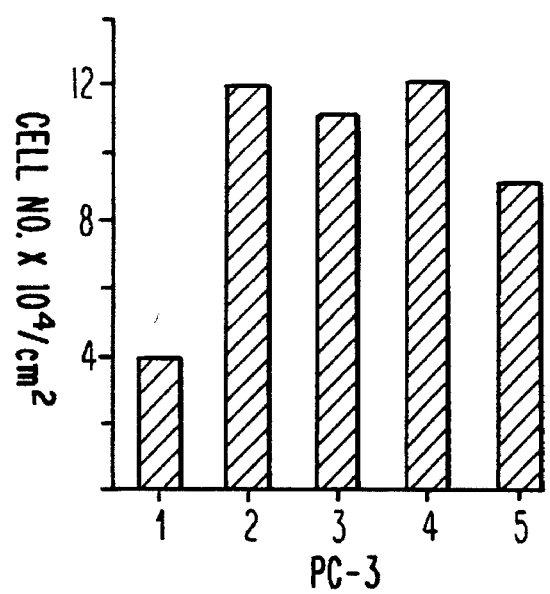
Figure 2:
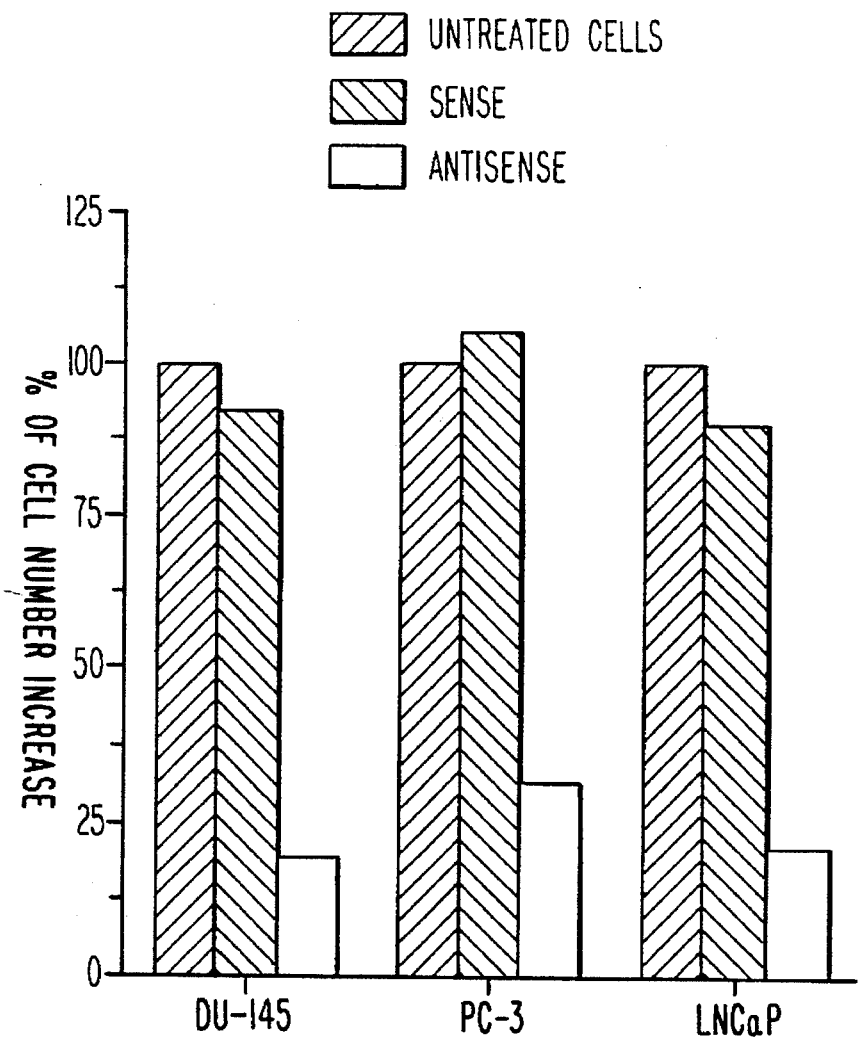
FIG. 2 is a schematic representation of the effect of antisense oligonucleotide to the IGF-1 receptor on the growth of prostatic cancer cell lines. Bars 1, 4, and 7 (control). Bars 2, 5, and 8 (sense). Bars 3, 6, and 9 (antisense).

In one series of experiments, well established cell lines that were adapted to grow in vitro and that originated from sources of human prostatic cancer are examined. The effect of individual growth factors on the growth of these prostatic cancer cell lines is shown in FIG. 1. The effect of an antisense oligodeoxynucleotide to the IGF-1 receptor RNA on the growth of these cells lines is shown in FIG. 2. The effects of antisense oligodeoxynucleotide to the IGF-1 receptor RNA on the growth of Balb 58 cells, human glioblastoma cells, human ovarian cancer cells, and HL-60 cells are also shown. As the data show, these cells need a functionally activated IGF-1 receptor for growth. Any cells having an IGF-1 receptor may be targeted by methods of the present invention. For example, leukemic cells, cancer cells, and smooth muscle cells may be targeted by methods of the present invention. The potential usefulness of such an antisense composition in the treatment of prostatic cancer and other forms of abnormal growth is shown by the observation that IGF-1 is a required growth factor. In other words, while the cells could circumvent other growth factor requirements by establishing an IGF-1/IGF-1 R autocrine loop, the activation of the IGF-1 receptor (IGF-1 R) is the last receptor-mediated event before DNA synthesis and mitosis, and presumably, cannot be circumvented except by intracellular substrates of the IGF-1 receptor. The experiments show that the IGF-1/IGF-1 receptor pathway plays an important role in the growth and differentiation of cancer cell lines and that antisense composition can inhibit their growth and cause differentiation.

Furthermore, methods of reversing transformed phenotype of cells with abnormal growth potential are provided by the present invention. For example, since the absence of IGF-1 receptor has been found to decrease cell growth by 70%, but completely inhibits the transformed phenotype, this approach can differentially affect cells having an abnormal phenotype, such as cancer cells, by reversing the transformed phenotype at concentrations of antisense that only partially affect normal growth. Reversal of the transformed phenotype causes differentiation that is usually irreversible. Furthermore, the cells may become immunogenic towards themselves providing an additional benefit.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

The invention is further illustrated by the following, non-limiting examples.

EXAMPLES

EXPERIMENT A

Example 1 Cell Lines

The following cells lines were used.
1) Balb/c 3T3 cells;
2) mouse embryo cells established as primary cultures from normal mouse embryo;

3) KO cells, established from littermate embryos, null for the IGF-1 receptor;

4) three human prostatic cancer cell lines obtained from the American Tissue Culture Collection: PC-3 (originating from a human adenocarcinoma of the prostate; ATCC# HTB81); LNCa.FGC ("LNC"; from a human metastatic adenocarcinoma of the prostate, ATCC# CRL1740); and DU-145 (from a human carcinoma of the prostate metastatic to the brain, ATCC# CRL1435);

5) a human ovarian carcinoma cell line, ON-CAR; ATCC# HTB161

6) Balb 58 cells, Porcu et al., *Mol. Cell. Biol.* 1992, 12, 5069–5077;

7) T98G cells, a glioblastoma cell line originating from a human glioblastoma; and 8) HL-60 cells, a well established human promyelocytic cell line.

Human prostatic cell lines were passaged as recommended by the ATCC; they are grown in the following serum free media: DU-145 in MEM supplemented with 1 µM ferrous sulfate, 1 mM sodium pyruvate and 0.1% bovine serum albumin (BSA). The same supplements were added to DMEM:RPMI 1640 (1:1) to grow PC-3 cells, and to RPMI 1640 for LNC cells.

Example 2 Growth in serum-free medium

The cells were plated first in 10% calf serum in order to provide attachment factor. Alternatively, poly-L-lysine may be used. Pietrzkowski et al., *Mol. Cell. Biol.* 1992, 12, 3883–3889. The growth medium was removed by careful and repeated washing after twenty four hours and replaced with serum-free medium, with the sole additions of bovine serum albumin (0.5 mg/ml) and ferrous sulfate, 1.0 µM. The number of cells was determined by standard methods at the times indicated in each individual experiment. All three cell lines, DU-145, PC-3, and LNC grow in serum-free medium as vigorously as in serum supplemented medium, unlike 3T3, p6 and human diploid fibroblasts which do not grow under serum-free conditions. Pietrzkowski et al., *Mol. Cell. Biol.* 1992, 12, 3883–3889.

Example 3 Effect of Growth Factors on Prostatic Cancer Cell Lines

Cells were cultured as described in Example 2. Epidermal growth factor (EGF) (20 ng/ml), platelet derived growth factor (PDGF) (1 ng/ml) or insulin-like growth factor-1 (IGF-1) (20 ng/ml) were added to individual cell cultures. No increase in cell growth was observed 96 hours after plating of DU-145 and PC-3 cell lines. The growth factors showed slight inhibitory effects on LNC cells 96 hours after plating.

Example 4 Reverse-Transcriptase Polymerase Chain Reaction (RT-PCR)

The prostatic cancer cell lines were tested for their ability to express IGF-1 receptor RNA by RT-PCR after incubation of cells in serum-free medium for 48 hours. Reverse-transcriptase polymerase chain reaction was performed by slight modification of the method of Rappolee et al., *J. Cell. Biochem.* 1989, 39, 1–11; Lipson et al., *Proc. Natl. Acad. Sci. U.S.A.* 1989, 86, 9774–9777. RNA was extracted from cells by slight modification of the method of Chomczynski and Sacchi, *Anal. Biochem.* 1987, 162, 156–159. Amplimers and probe for the IGF-1 receptor RNA were chosen on the basis of the published cDNA sequence of the human IGF-1 receptor. Ullrich et al., *EMBO J.* 1986, 5, 2503–2512. 5' amplimer, 5' ACC ATT GAT TCT GTT ACT TC 3' (SEQ ID NO: 1); 3' amplimer, 5' ATA CTC TGT GAC ATT CTT AA 3' (SEQ ID NO: 2); probe, 5' CTG CTC CTC TCC TAG GAT GA 3' (SEQ ID NO: 3). Labeling of probes and hybridization were carried out by standard methods as described for example by Feinberg and Vogelstein, *Anal. Biochem.* 1983, 132, 6–13 and Thomas, P. S., *Methods Enzymol.* 1983, 100, 255–266. The various controls used in the RT-PCR assays (elimination of DNA, rejection of samples that give signals without reverse transcriptase, and multiple amplification cycles) are described for example by Pietrzkowski et al., *Cell Growth & Diff.* 1992, 3, 199–205; Pietrzkowski et al., *Mol. Cell. Biol.* 1992, 12, 3883–3889; Reiss et al., *Oncogene* 1992, 7, 2243–2248. RNA amounts were monitored with amplimers and probe for the pHE 7 cDNA, ribosomal protein cDNA, whose cognate RNA is expressed constantly under different conditions of growth. Reiss et al., *Oncogene* 1992, 7, 2243–2248.

Figure 3:
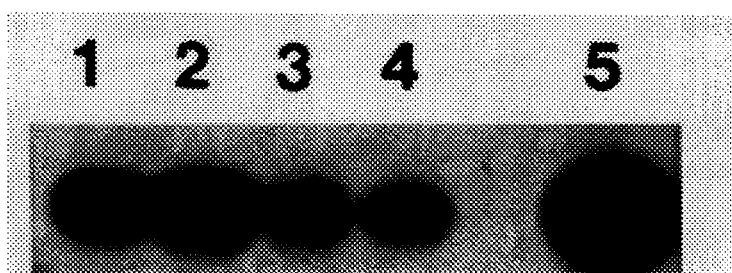
FIG. 3 is an autoradiogram of RT-PCR to determine the level of IGF-1 RNA produced by 5 different cell lines. Lane 1: PC-3; Lane 2: DU-145; Lane 3: LNC cells; Lane 4:WI-38 human diploid fibroblasts; Lane 5:p12 cells.

Results are shown in FIG. 3. RNAs from PC-3 cells (lane 1), DU-145 cells (lane 2), LNC cells (lane 3), WI-38 human diploid fibroblasts (lane 4, normal control) and p12 cells (which constitutively overexpress IGF-1 receptor RNA; lane 5) are shown. WI-38 cells and p12 cells were included as examples of cells which require IGF-1 for growth. Chomczynski, and Sacchi, *Anal. Biochem.* 1987, 162, 156–159.

Two of the cell lines, PC-3 and DU-145 express levels of IGF-1 receptor RNA that are about 10-fold (by densitometry) the levels in WI-38 cells. LNC cells express levels that are only slightly above those of WI-38. The amounts of RNA in each reaction were within 10% of each other.

Example 5 Antisense Experiments

Antisense and sense oligonucleotides corresponding to portions of codon –29 to –24 of the signal sequence of the human IGF-1 receptor preceding the proreceptor sequence, Ullrich et al., *EMBO J.* 1986, 5, 2503–2512 were prepared. The oligodeoxynucleotides were synthesized on an Applied Biosystem Model 391 EP DNA synthesizer using β-cyanoethyl phosphoramidite chemistry. Pietrzkowski et al., *Cell Growth & Diff.* 1992, 3, 199–205; Pietrzkowski et al., *Mol. Cell. Biol.* 1992, 12, 3883–3889; Reiss et al., *Oncogene* 1992, 7, 2243–2248.

Phosphorothioate oligonucleotides having sequences corresponding to codons –29 to –24 of the signal sequence, having the sequences TCCTCCGGAGCCAGACTT (SEQ ID NO: 4; antisense) and GCACCGGGAAGTTGTGTCAA (SEQ ID NO: 6; mismatched) were prepared as described above. 40 µg/ml of the oligonucleotides were added to SV-40 transformed Balb 58 cells (L clone; Porcu et al., *Mol. Cell. Biol.* 1992, 5069–5077), in 1% serum at 34° C. The cells were counted after 72 hours. The antisense oligonucleotide caused an 85% inhibition of cell growth as compared to a control (no addition of oligonucleotide). The mismatched antisense oligonucleotide resulted in only a 15% inhibition of cell growth.

Three human prostatic cancer cell lines were also treated with antisense phosphorothioate oligonucleotides. The oligonucleotides had the sequences TCCTCCGGAGCCAGACTT (SEQ ID NO: 4; antisense) and AAGTCTGGCTCCGGAGGA (SEQ ID NO: 5; sense). Pietrzkowski et al., *Cell Growth & Diff.* 1992, 3, 199–205. The oligodeoxynucleotides were added to the medium after 48 hours in serum-free medium (40 µg/ml) and the treatment was repeated the next day (20 µg/ml). The cells were counted 48 hours after the second addition. FIG. 2 shows that antisense oligonucleotides to IGF-1 receptor RNA markedly inhibited all three prostatic cancer cell lines, the inhibition varying from 70 to 90%. After 48 hours treatment, the prostatic cancer cells look flat, polygonal, with the characteristics of a normal epithelial cell.

Antisense studies were also carried out on an ovarian carcinoma cell line and on a glioblastoma cell line. The results are summarized in TABLE 1.

TABLE 1

Effect of Antisense Oligodeoxynucleotides to the IGF-1 Receptor RNA on the Growth of Human Cancer Cell Lines

| cell lines | Inhibition of growth % | |
|---|---|---|
| | antisense | sense |
| T98G (human glioblastoma) | 90 | 12 |
| ON-CAR (human ov.ca.) | 100 | 2 |

Cells were grown in serum-free medium supplemented with individual growth factors and the antisense or sense phosphorothioate oligonucleotides at concentrations of 40 µg/ml. The oligonucleotides had the sequences TCCTCCGGAGCCAGACTT (SEQ ID NO: 4; antisense) and AAGTCTGGCTCCGGAGGA (SEQ ID NO: 5; sense). The inhibition is based on the growth of control cells (no oligos added). Cells treated with antisense showed signs of differentiation, with flattening, contact inhibition and reversal of the transformed phenotype.

HL-60 cells were also treated with the antisense phosphorothioate oligonucleotides. The oligonucleotides had the sequences TCCTCCGGAGCCAGACTT (SEQ ID NO: 4; antisense) and AAGTCTGGCTCCGGAGGA (SEQ ID NO: 5; sense). When HL-60 cells were treated with antisense oligonucleotides to the IGF-1 receptor RNA, the cells differentiated toward a macrophage lineage, just as when they are treated with a differentiating agent.

Example 6 Autophosphorylation of the IGF-1 Receptor

Figure 4:
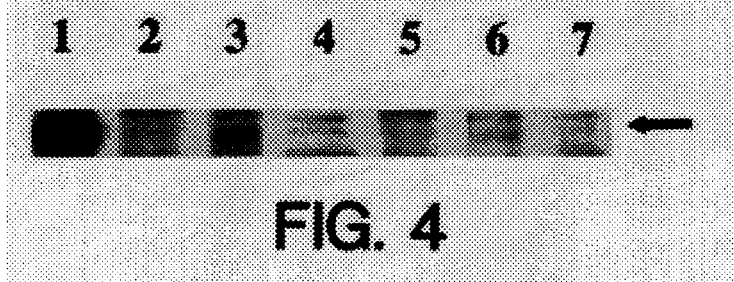
FIG. 4 is a western blot showing autophosphorylation of IGF-1 receptor. Lane 1:p12 cells 48 hours in serum-free medium, Lanes 2–4: PC-3, DU-145, and LNC cells respectively, 48 hours in serum-free medium 15 minutes after the addition of IGF-1 (3 ng/ml), Lanes 5–7: PC-3, DU-145 and LNC cells respectively, 48 hours in serum-free medium, no added IGF-1.

The cells were characterized for levels of IGF-1 receptor that can be autophosphorylated by IGF-1. Autophosphorylation was carried out by slight modification of the method of Lammers et al., *EMBO J.* 1989, 8, 1369–1375, using the monoclonal antibody to the IGF-1 receptor available from Oncogene Sciences (Uniondale, N.Y.), an anti-phosphotyrosine antibody available from UBAI (Saranac Lake, N.Y.), and the ECL detection system kit from Amersham (Arlington Heights, Ill.). Protein lysates were obtained from cells growing for 48 hours in serum free medium. Before lysis, the cells were treated for 2 hours with sodium orthovanadate (1 mM). Results are shown in FIG. 4.

Although the amount of autophosphorylated IGF-1 receptor is not as high as in p12 cells (lane 1), which constitutively overexpress the human IGF-1 receptor, substantial amounts of receptor that can be autophosphorylated by IGF-1 are detectable in all cell lines (lanes 2–4). More significantly, the auto-phosphorylation of the receptor can be detected in cells growing in serum-free medium even without the addition of IGF-1 (lanes 5–7), indicating that, in these cell lines, the IGF-1 receptor is constitutively autophosphorylated due to the presence of measurable amounts of IGF-1 secreted by the cells themselves into the medium.

Example 7 IGF-1 Radioimmune Assay

The ability for the cells to produce and secrete IGF-1 in the medium was determined by radioimmune assay. The radioimmune assay was performed essentially as described by Pietrzkowski et al., *Mol. Cell. Biol.* 1992, 12, 3883–3889. Cells were incubated in serum-free medium for 72 hours. Conditioned medium containing 1% bovine serum albumin (BSA) and 1 mM ferric sulfite was collected at various times after the cells were transferred to serum-free medium. To remove IGF-1 binding proteins, 0.1 ml of conditioned medium was mixed with 900 ml of 1 M acetic acid and 5% BSA and loaded onto SepPak C18 columns (Waters, Milford, Mass). Before loading, the column was washed with 10 ml of methanol and then by 10 ml $H_2O$. After loading, the column was washed with 10 ml of 4% acetic acid, and IGF-1 was eluted in 1 ml of 50% acetonitrile and 4% acetic acid. After lyophilization, the sample was resuspended directly in 100 ml of radioimmunoassay buffer. The assay was performed with a rabbit IGF-1 anti-serum and a second antibody bound to magnetic beads (Amersham, Arlington Heights, Ill.) using a commercially available radioimmunoassay kit (Amersham, Arlington Heights, Ill.). The results are shown in TABLE 2.

TABLE 2

| Cell Line | Amount of IGF-1 in ng IGF-1/ml/$2 \times 10^6$ cells |
| --- | --- |
| DU-145 | 12.06 |
| LNC | 14.38 |
| PC-3 | 24.36 |

As seen in TABLE 2, all three cell lines are good producers of IGF-1, especially PC-3. In all instances, however, the concentration of IGF-1 is more than sufficient to autophosphorylate the IGF-1 receptor and to sustain growth if the number of IGF-1 receptors is adequate.

For example, ordinarily, in cells expressing an adequate number of IGF-1 receptors, like p6 cells, 3.0 ng/ml of IGF-1 are sufficient to induce autophosphorylation of the receptor and stimulation of growth.

Example 8 SV40 T antigen

For transformation, pts58H, a plasmid which contains the tsA58 T antigen coding gene, cloned in pBR322, was used as well as the hygromycin resistance hph cDNA under the control of a viral promoter. Porcu et al., *Mol. Cell. Biol.*, 1992, 12, 5069–507. Clones of cells transfected with this construct are selected in hygromycin.

KO cells (no IGF-1 receptors) grow in 10% serum at a rate that is roughly 40% the rate of wild type cells (MEC cells). IAs shown in FIG. 5, panel A, these cells are indicated as K10 and C2 cells. Both MEC and KO cells were transfected with the plasmid tsA58H, carrying the SV40 T antigen and a selectable marker. Clones were selected in hygromycin; because of the plasmid used, all cells in all clones were 100% T antigen positive.

FIG. 5, Panel B, shows the growth characteristics of these two types of cells, transfected with T antigen, and which we call KI 0a58 and C2a58. The figure gives the saturation density of these two cell lines. The saturation density of C2a58 cells is 4-fold the saturation density of KI 10a58. The latter one formed a contact-inhibited monolayer, while C2a58 cells were forming foci, like transformed cells. This suggests that T antigen has not been able to fully transform the KO cells.

Example 9

Soft agar assay was carried out by standard methods. A more convincing way to test for transformation is to grow cells in soft agar, a test that has been used for many years to characterize transformed cells. Untransformed cells do not form colonies in soft agar; only transformed cells can form colonies, and the number of colonies formed is usually taken as an index of transformation. Cells were tested in soft agar, and the results of such an experiment are shown in TABLE 3.

TABLE 3

Growth in Soft Agar of Various Cell Lines

| cell line | number of colonies formed |
| --- | --- |
| Balb/c 3T3 cells | 0 |
| Balb58 cells(transformed 3T3) | >200 |
| T98G (human glioblastoma) | >100 |
| MEC cells | 0 |
| KO cells | 0 |
| T-MEC cells(T transformed) | >200 |
| T-KO cells(T-transfected) | 0 |

One thousand cells of each cell line were seeded and the number of colonies determined after 2 weeks.

The prostatic cancer cell lines and the ovarian carcinoma cell line also grow in soft agar, as reported by other investigators. TABLE 3 clearly show that a strong oncogene like SV40 T antigen is incapable of transforming cells that do not have IGF-1 receptors. Experiments are in progress in nude mice: preliminary data indicate, as anticipated, that T-KO cells do not grow in nude mice, whereas other T-transformed mouse cells do.

EXPERIMENT B

Example 10—Cell Cultures and Plasmid Construction

Mouse embryos were dissected from anesthetized females at day 18 of gestation and genotyped using DNA prepared from the mouse tails by Southern analysis as described by Liu, et al., *Cell*, 1993, 75:59 and Baker et al., *Cell*, 1993, 75:73. Wild-type and homozygous IGF-1 receptor mutant (Igf1r (-1-)) littermates were used for establishing primary cultures of embryonic fibroblasts as described by Warton, et al., in *Cell Growth and Division*, 1989, 139–153, Baserga, ed, IRL Press, Oxford, England.

The embryos were minced, and treated with trypsin for 15 minutes. The cells of the resulting suspension were plated onto 100 mm culture dishes and cultured in Dulbecco's modified Eagle's medium (DMEM:GIBCO-BRL, Grand Island, N.Y.) supplemented with 10% fetal bovine serum. The cultures were maintained at subconfluent levels by trypsinizing every three days and reseeding at a density of $1.5 \times 10^3$ cells/$cm^2$, following the same protocol used to generate 3T3 cell lines. Todaro, et al., *J. Cell Biol.*, 1963, 17, 299. Primary cultures underwent crisis following 2–4 weeks in culture. Crisis results in immortalized cells. Cells null for IGF-1 receptor, R-, cultures entered crisis later than the wild-type cells due to the relatively slow doubling rate.

Cells from wild-type and homozygous Igf1r (-1-) mutant embryos were established initially as primary cultures and subsequently as post-crisis cell lines, which will be referred to as parental lines W and R-, respectively.. These lines, which were derived by a protocol previously used to generate 3T3 cells, have a fibroblast-like appearance. Todaro, G. J. et al., *J. Cell Biol.*, 1963, 17:299. In serum-free medium supplemented with PDGF (5 ng/ml), EGF (20 ng/ml) and IGF-1 (20 ng/ml), W cells grow well, while R- cells fail to increase in number. Growth of R- cells can be sustained in 10% serum, but their growth rate is only 40-50% that of W cell controls (see TABLE 4). The growth of W cells under the conditions of TABLE 4 is essentially the same as that of the Balb/c 3T3 cells.

TABLE 4

GROWTH OF W AND R- CELLS IN CULTURE

| CELL TYPE | GROWTH FACTORS | NUMBER OF DOUBLINGS |
|---|---|---|
| W Cells | PDGF, EGF, IGF-1 | 1.5 |
| W Cells | 10% serum | 3.0 |
| W Cells | serum-free medium | 0 |
| R- Cells | PDGF, EGF, IGF-1 | 0 |
| R- Cells | 10% serum | 1.5 |
| R- Cells | Serum-free medium | 0 |

Cells were seeded at a concentration of $5 \times 10^3$ cells/cm$^2$ in plastic dishes, in DMEM supplemented with 10% fetal calf serum. After 24 hours, the growth medium was removed, the cells washed several times with Hanks' solution and DMEM was added with the indicated supplements. Cells were counted at 48 and 72 hours after changing to the indicated condition. The number of doublings shown represents 72 hours.

Indirect biochemical analysis showed that a functional IGF-1R is absent from primary cultures of cells isolated from day 14.5 Igf1r (-1-) mutant embryos. Liu, et al., *Cell*, 1993, 75:59 and Baker et al., *Cell*, 1993, 75:73. To confirm this result using a specific antibody and establish unequivocally that R- cells are completely devoid of IGF-1 receptor, the following experiment was performed.

After incubation in the presence of IGF-1 for ligand-activated autophosphorylation of the IGF-1 receptor, R- cells and control W cells were lysed and a polyclonal antibody against the β subunit of mouse IGF-1 receptor was added to immunoprecipitate and functional IGF-1 receptor present in the lysate. The precipitated proteins were solubilized in the presence of β-mercaptoethanol, resolved electrophoretically and transferred to a nitrocellulose membrane. The β subunit of IGF-1 receptor autophosphorylated in an IGF-1-dependent fashion, was visualized by immunostaining with an anti-phosphotyrosine antibody (UBL, Saranac Lake, N.Y.) and recognized by size, and by the response to IGF-1. The apparent molecular weights of the α and β subunits of IGF-1 receptor resolved electrophoretically after disulfide bond reduction and denaturation are 135 kD and 97 kD, respectively. Autophosphorylation of β subunit (97 kD species) was detected, after IGF-1 stimulation, in W cells, but not in R- cells.

For confirmation the presence of the β subunit of the IGF-1 receptor was examined by cross-linking radioiodinated IGF-1 to cell membranes, followed by electrophoretic analysis and autoradiography. Yamori, et al., *Cancer Res.*, 1991, 51, 5859. A labeled protein of 135 kD was easily detectable in W cells, and its signal could be eliminated by competing the radioiodinated ligand with a 1,000 fold excess of unlabeled IGF-1. In contrast, it was not possible to detect a labeled protein species of this size in R- cells, even after significant overexposure of the autoradiogram.

Figure 6:
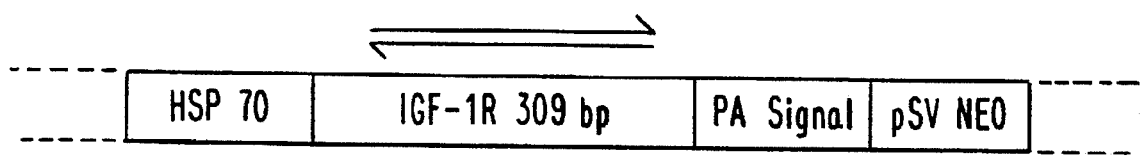
FIG. 6 is a diagram of the plasmid constructs IGF-1RS and IGF-1RAS.

T98G cells are a human glioblastoma cell line, that produces large amounts of IGF-1. Stein, G. H., *J. Cell. Physiol.*, 1979, 99:43. Two other cell lines were generated from T98G cells, expressing, respectively, a sense and an antisense RNA to the human IGF-1 receptor RNA. Expression plasmids which generate mRNA sequences, sense or antisense to the human IFG-1 receptor, were constructed. The human heat shock promoter HSP 70 was excised from the pSp2 (Craig et al., *Cell*, 1979, 16:575) with PstI and inserted into the SalI site of the pUC 18 multiple cloning site (MCS). The hepatitis B polyadenylation (PA) signal sequence and a neomycin resistance gene under control of the simian virus 40 (SV40) promoter were cloned into the BamHI site of the multi-cloning site to generate the plasmid HSP-neo. An XbaI-XhoI fragment corresponding to the bp 1-309 of the IGF-1 receptor cDNA (Ullrich et al., *EMBO J.* 1986, 5, 2503-2512) was filled-in with Klenow, and blunt end ligated into a filled-in BamHI site of the plasmid HSP-neo. The resulting plasmids were restricted and sequenced to determine the orientation of the transcripts. The plasmids predicted to produce the sense and antisense transcripts of the IGF-1 receptor cDNA were named HSP-IGF-1RS and HSP-IGF-1RAS, respectively, see FIG. 6. Transfections were performed using the calcium phosphate precipitation method (Shen et al., *Mol. Cell. Biol.*, 1982, 2:1145). After 48 hours, 1 mg/ml neomycin was added to the cells to obtain stable transfectants.

Cells were seeded at a density of $3 \times 10^3/35$ mm plate in 10% serum on a top layer of 0.3% agar and a bottom support layer of 1% agar. Colonies of greater than 10 cells were counted 14-21 days later.

C6 cells are a rat glioblastoma cell line. Trojan et al., *PNAS*, 1992, 89:4874 and Trojan et al., *Science*, 1993, 259:94.

Example 11—Plasmid Transfection

Cells were transfected with DNA of the following plasmid constructs: a) ptsA58H (Porcu, et al., *Mol. Cell. Biol.*, 1992, 12:5069) which contains the hygromycin-resistance gene (hyg) and the sequence encoding tsA58, a temperature-sensitive SVLT (Tegtmeyer, *J. Virol.*, 1975, 15:613); b) pSV2G (Floros, et al., *Exp. Cell Res.*, 1981, 132:215), which contains the sequence encoding the wild-type SV40 T antigen and which was co-transfected with a plasmid containing the hygromycin resistance gene (LHL4) (Gritz, et al., *Gene*, 1983, 25:179); and c) Cvn-IGF-1 receptor, which contains the neomycin resistance gene (neo) and the entire coding sequence of the human IFG-1 receptor cDNA, both of which are under control of the SV40 promoter; as described by Porcu, et al., *Mol. Cell. Biol.*, 1992, 12, 5069.

Primary cultures were extremely sensitive to hygromycin and selection was carried out in 10 μg/ml of hygromycin. Cell proliferation in anchorage-dependent conditions was assayed by trypsinizing the cells and counting in triplicate every 24 hours, using a hemocytometer.

Parental W and R- cells were transfected with DNA of a plasmid construct ptsA58H (Porcu, et al., *Mol. Cell. Biol.*, 1992, 12, 5069), containing a selectable marker, the hygromycin-resistance gene (Gritz et al., *Gene*, 1983, 25:179), and the sequence encoding the temperature-sensitive SV40T antigen tsA58 (Tegtmeyer, *J. Virol.*, 1975, 15:613). Cells expressing tsA58 are transformed at the permissive temperature of 34 C., but revert to the untransformed phenotype at the restrictive temperature of 39.6 C. (Porcu et al., supra, Lammers, et al., *EMBO J*, 1989, 8:1369, Jar, et al., *Mol. Cell. Biol.*, 1989, 9:1672, Radna et al., *Molc. Cell. Biol.*, 1989, 9:3093, and Resnick-Silverman et al., *J. Virol.*, 1991, 65:2845). Since the selectable marker and T antigen are expressed from the same plasmid, all of the hygromycin-resistant clones derived were also T-positive. Thus, when selected W and R- cells harboring ptsA58H were examined by immunofluorescence using an antibody against T antigen, both cell-types exhibited approximately the same level of intensity in staining (45±0.9 and 43.7±0.7 arbitrary densitometric units respectively). These transfected derivatives of the parental W and R- lines were designated (tsA)W and (tsA)R- cells.

The four types of cells [W, R-, (tsA)W and (tsA)R-] were plated and grown in DMEM supplemented with 10% serum for 5 days, and then cell numbers were determined to assess saturation densities. As expected from previous results, the ratio of R- to W cell numbers was 0.53. However, growth was differentially stimulated by the presence of SVLT. The number of (tsA)W cells was 2.7 fold higher than that of W cells, while (tsA) R- cells grew only 30% above the saturation density of the R- parent. More importantly, the (tsA) W cells were overtly transformed, as evidenced by the appearance of large foci, while the (tsA)R- cells continued to be contact-inhibited. Identical results were obtained with several different T positive clones derived from the parental cell lines.

To further assess the presence or absence of a transformed phenotype, we used soft-agar assays (Thompson, et al., Virology, 1990, 178:15). The results of a typical experiment are shown in TABLE 5. As expected, (tsA)W cells formed colonies in soft agar in numbers increasing with the number of cells that were seeded, while only a single small colony of 12 cells appeared with the highest number of plated (tsA)R- cells. The cells were maintained in 10% serum for more than 3 weeks, which is a more than adequate time period for establishment of colonies in soft agar even at reduced growth rates. Therefore, the (tsA)R- cells do not have potential for colony formation in soft agar.

TABLE 5

GROWTH IN SOFT AGAR OF MOUSE EMBRYO CELLS EXPRESSING SVLT

| CELL TYPE | SEEDING DENSITY × 10³ | NUMBER OF COLONIES |
|---|---|---|
| (tsA)W | 1 | 8 |
| (tsA)W | 10 | 64 |
| (tsA)W | 100 | 350 |
| (tsA)R- | 1 | 0 |
| (tsA)R- | 10 | 0 |
| (tsA)R- | 100 | 1 |
| (wtT)W | 10 | 58 |
| (wtT)W | 100 | 154 |
| (wtT)R- | 10 | 0 |
| (wtT)R- | 100 | 0 |
| (tsA)R+ | 10 | 16 |
| (tsA)R+ | 100 | 70 |

(tsA)W and (tsA)R- are, respectively, W and R- cells expressing the tsA58 T antigen. The same embryo cells expressing the wt T antigen are designated (wtT). (tsA)R+ cells are (tsA)R- cells expressing a stably transfected human IGF-1 receptor cDNA. Parental cell lines, W and R- did not grow in soft agar. Cells were seeded at the indicated densities and colonies were counted after 25 days in culture. Numbers are averages of duplicate counts of a single experiment. Several assays were performed with reproducible results for each cell line. Several clones of (tsA) and (wtT) cells were also tested with similar results.

To exclude the possibility that the temperature-sensitive T antigen is somehow different from wild-type, additional lines were derived from the parental W and R- cells by co-transfecting two plasmids expressing wild-type SVLT and the hygromycin-resistance gene, respectively. Following hygromycin-selection, cells testing positive for T antigen expression were expanded into clones that were assayed for colony formation in soft agar. Again, in contrast to controls, the derivatives of R- cells were unable to form colonies, TABLE 5.

TABLE 6

GROWTH IN SOFT AGAR OF GLIOBLASTOMA CELL LINES TREATED BY ANTISENSE STRATEGY TO THE IGF-1 RECEPTOR

| CELL TYPE | SEEDING DENSITY × 10³ | NUMBER OF COLONIES |
|---|---|---|
| T98G-sense | 3 | 305 |
| T98G-antisense | 3 | 5 |
| C6 | 3 | 280 |
| C6-sense | 3 | 230 |
| C6-antisense | 3 | 115 |

Cells were seeded at the indicated densities and colonies were counted after 14 days in culture. Both cell lines showed a consistently higher efficiency of colony formation than t-antigen transfected mouse embryo cells.
The T98G cells used are lines which have been stably transfected with a heat shock promoter construct which transcribes either a sense or antisense transcript for the first 309 bp of the IGF-1 receptor. The T98G cells containing the antisense construct grew at 40–50% of the rate of the lines containing the sense construct.
The C6 cell line was treated with 80 µg/ml of antisense oligonucleotide to the IGF-1 receptor known to reduce the level of IGF-1 receptor at the cell surface (Pietrzkowski, et al., Cell Growth and Diff., 1992, 3:199). The sequence used corresponds to the first 18 bp after the ATG initiation codon of the IGF-1 receptor cDNA. the addition of the antisense oligonucleotide had very little effect on the anchorage dependent growth of these cells in 10% serum.

An additional experiment was performed to show that the ability of SVLT to transform fibroblasts depends directly on the presence of functional IGF-1 receptor. This experiment was based on the observation that cells expressing IGF-1 receptor constitutively are able to grow in serum-free medium supplemented with IGF-1 or insulin at supraphysiological concentrations (Pietrzkowski, et al., Cell Growth and Diff., 1992, 3:199, McCubrey, et al., Blood, 1991, 78:921). Thus, one of the (tsA)R- clones was transfected with a plasmid (Cvn-IGF-1 receptor) expressing the full-length coding sequence of human Igf1r cDNA and also the neomycin-resistance gene, both under the control of the SV40 promoter (Ullrich, et al., EMBO J, 1986, 5:2503). Clones selected directly in serum-free medium supplemented with insulin (20 µg/ml) were picked; under these conditions, only clones constitutively expressing the IGF-1 receptor can grow (Pietrzkowski, et al., supra). By autophosphorylation analysis, these clones expressed IGF-1 receptor at levels comparable to those of Balb/c 3T3 cells. these clones were able to form colonies efficiently in soft agar, without the addition of IGF-1. The endogenously-produced T antigen, which was previously ineffective, attained its transforming potential once the cells acquired constitutively-expressed human IGF-1 receptor.

Example 12—Immunostaining for Large T Antigen

Cells fixed in cold methanol were incubated with a 1:10 dilution of anti-large T antigen antibody (PAb 419; Oncogene Science, Uniondale, N.Y.) then stained with a 1:100 dilution of a fluorescinated goat antimouse immunoglobulin G antibody (Oncogene Science). Staining intensity was measured in arbitrary units by computer analysis of photographic images of the stained cells.

Example 13—Soft Agar Assay

Anchorage-independent growth was assayed by scoring the number of colonies formed in 0.2% agarose (with either a 1% or 0.4% agarose underlay). T antigen transfected cells were allowed to grow for three weeks while glioblastoma cell colonies were counted after two weeks due to the higher growth rate of these cells relative to the T antigen-transformed cells.

Previous indirect data, showing that NIH 3T3 cells overexpressing IGF-1 receptor grow in soft agar in the presence of the ligand (Kaleko, et al., *Mol. Cell. Biol.*, 1990, 10:464) and that the tumorigenicity of the rat glioblastoma C6 cell line is abrogated by antisense Igf-1 RNA (Trojan et al., supra) are consistent with the results obtained with mutant cells lacking IGF-1 receptor. These results suggest that IGF-1 receptor mediates signaling of IGF-1 is an indispensable component of the operation of a transformation pathway. To show that this is the case, an antisense RNA strategy was performed with C6 cells and also with cells of an additional glioblastoma cell line, T98G (Stein, supra), which grow well in 1% serum.

T98G glioblastoma cells were transfected with appropriate constructs, to derive cell lines expressing either antisense or (control) sense human Igf1r RNA. Soft agar assays using these derivatives showed that, in comparison to the control cells, the number of colonies formed by 98G cells expressing Igf1r antisense RNA was reduced more than 60-fold, see TABLE 6. In an analogous experiment, C6 cell colony formation in soft agar was reduced 2-fold in the presence of an antisense oligodeoxynucleotide inhibiting Iglfr mRNA, see TABLE 6. The growth of C6 cells in culture dishes was not reduced more than 10% in the presence of the same concentration of antisense oligodeoxynucleotides, while the growth rate of T98G cells expressing antisense RNA was 40% of that of wild-type cells or cells expressing sense RNA. These observations suggest that the transformation phenotype is more sensitive to the abrogation or diminution of IGF-1 receptor function than the inhibition of growth.

Example 14—Cross-Linking of IGF-1 Receptor

Radioiodinated IGF-1 was cross-linked to the IGF-1 receptor using disuccinimidyl suberate as described by Yamori, et al., *Cancer Res.*, 1991, 51, 5859. After cross-linking, the proteins were resolved on an 8% polyacrylamide gel and the dried gel exposed to X-ray film (Kodak X-OMAT) for autoradiography.

Example 15—Antisense Oligonucleotides

The antisense and sense oligodeoxynucleotides to the IGF-1 receptor mRNA used for the colony formation assay of C6 cells were prepared according to Pietrzkowski, et al., *Cell Growth and Diff.*, 1992, 3, 199. They correspond to the 18 bp sequence following the ATG of the IGF-1 receptor cDNA. The antisense oligonucleotides were added to the cells at the time of seeding at a concentration of 80 μg/ml.

Example 16—In vivo Experiments Performed in Rats

Three C6 cell lines were prepared. C6 cell lines were separately transfected with expression vectors capable of expressing sense or antisense oligonucleotides, respectively, to IGF-1 receptor RNA. Plasmids were prepared as described above. Wild type or untransfected C6 cells were also grown in culture. Cell lines were established by transfection of C6 with HSP70 promoter driving 305 bp of IGF-1 receptor RNA cell lines established by transfection. The cells carried a neomycin resistance gene. The cells were selected with G418 and monitored for IGF-1 receptor expression.

Rats were subcutaneously injected in the flank, i.e. side, with one of the three C6 rat glioblastoma cell lines at a concentration of $10^7$. This tumor grows vigorously in rats, reaching large sizes and eventually killing the animals. Rats injected with wild type cells resulted in tumors of about 1–2 cm.

Tumors resulted in rats injected with wild type cells and with cells expressing sense oligonucleotides, 27/27 rats injected with wild type cells and 12/12 rats injected with sense oligonucleotides, see TABLE 7. However, none of the 24 rats injected with antisense oligonucleotides yielded tumors, see TABLE 7.

In another experiment, animals were first injected with cells expressing sense oligonucleotides, prepared as set forth above, at a concentration of $10^7$. Six days later, the same animals were injected with wild type cells, at a concentration of $10^7$, and 6 of the 6 rats resulted in bilateral tumor development. None of the rats injected with antisense oligonucleotides initially and then wild type cells resulted in tumor development, see TABLE 7.

Another experiment injected wild type and sense expressing cells simultaneously, or wild type and antisense simultaneously. All of the rats given sense oligonucleotides (3/3) revealed tumors while 0/3 of the rats receiving antisense oligonucleotides had tumor development, see TABLE 7.

In anther experiment, fifteen rats were injected with wild type cells initially followed two weeks later with antisense oligonucleotides. Autopsies revealed (all injection concentrations were $10^7$ cells) complete tumor regression; the tumors disappeared. Significantly, the antisense oligonucleotides were injected into the flank opposite the wild type injection, TABLE 7.

TABLE 7

Effect of IGF-IR Sense and Antisense RNA on Tumor Induction in Rats

| Injection #1 (right) | Injection #2 (left) | Tumor Development number of animals |
|---|---|---|
| Wild-sense | n/a | 27/27 |
| Sense | n/a | 12/12 |
| Antisense | n/a | 0/24 |
| Sense | Wild-type (day 6) | 6/6 bilaterally |
| Antisense | Wild-type (day 6) | 0/6 |
| Wild-type | Sense (simultaneous) | 3/3 bilaterally |
| Wild-type | Antisense (simultaneous) | 0/3 |
| Wild-type | Antisense (2 weeks) | complete tumor regression in right flank, 15/15 |

The data resulting from the in vivo rat experiments identified above is significant for application to human cancers. The rat tumors in the above identified experiments were syngeneic. The tumors originated in these rats, the tumors are not foreign and the data is therefore the data is not the result of rejection of these tumors by the rats.

Various modifications of the invention in addition to those shown and described herein will be apparent to those skilled in the art from the foregoing description. Such modifications are also intended to fall within the scope of the appended claims.

What is claimed is:

1. An antisense oligonucleotide consisting of the nucleotide sequence shown as SEQ ID NO:4.

2. The antisense oligonucleotide of claim 1 wherein said oligonucleotide comprises at least one phosphorothioate internucleotide linkage.

3. A method of inhibiting cancer cell proliferation comprising contacting cancer cells in vitro with an antisense oligonucleotide consisting of the nucleotide sequence shown as SEQ ID NO:4.

4. The method of claim 3 wherein said oligonucleotide comprises at least one phosphorothioate internucleotide linkage.

* * * * *